United States Patent
Beeckler et al.

(10) Patent No.: US 10,589,060 B2
(45) Date of Patent: Mar. 17, 2020

(54) EXTRUSION WITH PREFERENTIAL BEND AXIS

(71) Applicant: Biosense Webster (Israel) Ltd., Yokneam (IL)

(72) Inventors: Christopher Thomas Beeckler, Brea, CA (US); Joseph Thomas Keyes, Glendora, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 219 days.

(21) Appl. No.: 15/386,514

(22) Filed: Dec. 21, 2016

(65) Prior Publication Data

US 2018/0169376 A1   Jun. 21, 2018

(51) Int. Cl.
*A61M 25/00* (2006.01)
*B29C 48/11* (2019.01)
(Continued)

(52) U.S. Cl.
CPC ...... *A61M 25/0012* (2013.01); *A61M 25/005* (2013.01); *A61M 25/0045* (2013.01); *A61M 25/0054* (2013.01); *B29C 48/0015* (2019.02); *B29C 48/0021* (2019.02); *B29C 48/09* (2019.02); *B29C 48/11* (2019.02);
(Continued)

(58) Field of Classification Search
CPC .......... A61M 25/0012; A61M 25/0045; A61M 25/0054; A61M 25/005; A61M 25/0053; A61M 25/0144; B29C 47/065; B29C 47/021; B29C 47/0064; B29C 47/064; B29C 47/005; B29C 47/0028; B29C 47/0023; B29C 47/02; B29C 48/15; B29C 48/20; B29C 48/19; B29C 48/0015; B29C 48/09; B29C 48/151; B29C 48/21; B29C 48/11; B29C 48/0021; B29L 2031/7542; B29K 2077/00; B29K 2995/0082; B29K 2071/00

See application file for complete search history.

(56) References Cited

U.S. PATENT DOCUMENTS

| 4,521,359 A | 6/1985 | Tsien |
| 4,888,146 A | 12/1989 | Dandeneau |

(Continued)

FOREIGN PATENT DOCUMENTS

| EP | 1787674 A1 | 5/2007 |
| EP | 2301617 A1 | 3/2011 |

(Continued)

OTHER PUBLICATIONS

Extended European Search Report for European Application No. EP17209464, dated May 4, 2018; 9 pages.

*Primary Examiner* — Jeffrey M Wollschlager
(74) *Attorney, Agent, or Firm* — Roberts Calderon Safran & Cole, P.C.

(57) ABSTRACT

A catheter is made by coextruding first and second molten polymers, wherein the second molten polymer forms a flexible inner core and the first molten polymer forms exactly two bands on opposite sides of the inner core. The inner core is braided, and a third molten polymer extruded onto the braid to form a flexible jacket that encloses the braid, the bands and the inner core. The bands are more rigid than the inner core, and they provide preferential in-plane bending.

7 Claims, 2 Drawing Sheets

(51) Int. Cl.
*B29C 48/21* (2019.01)
*B29C 48/00* (2019.01)
*B29C 48/151* (2019.01)
*B29C 48/15* (2019.01)
*B29C 48/09* (2019.01)
*B29C 48/19* (2019.01)
*B29C 48/20* (2019.01)
*A61M 25/01* (2006.01)
*B29K 71/00* (2006.01)
*B29K 77/00* (2006.01)
*B29L 31/00* (2006.01)

(52) U.S. Cl.
CPC ............ *B29C 48/15* (2019.02); *B29C 48/151* (2019.02); *B29C 48/19* (2019.02); *B29C 48/20* (2019.02); *B29C 48/21* (2019.02); *A61M 25/0053* (2013.01); *A61M 25/0144* (2013.01); *B29K 2071/00* (2013.01); *B29K 2077/00* (2013.01); *B29K 2995/0082* (2013.01); *B29L 2031/7542* (2013.01)

(56) References Cited

U.S. PATENT DOCUMENTS

| | | | | |
|---|---|---|---|---|
| 5,199,950 | A * | 4/1993 | Schmitt | A61M 25/0144 600/585 |
| 5,348,536 | A * | 9/1994 | Young | A61M 25/0009 264/171.27 |
| 5,356,709 | A | 10/1994 | Woo et al. | |
| 5,439,454 | A | 8/1995 | Lo et al. | |
| 5,453,099 | A * | 9/1995 | Lee | A61L 29/085 604/264 |
| 5,456,674 | A * | 10/1995 | Bos | A61M 25/0009 604/526 |
| 5,538,510 | A | 7/1996 | Fontirroche et al. | |
| 5,891,114 | A * | 4/1999 | Chien | A61M 25/0053 138/123 |
| 5,944,691 | A * | 8/1999 | Querns | A61B 17/3439 604/104 |
| 5,993,462 | A | 11/1999 | Pomeranz et al. | |
| 6,041,153 | A * | 3/2000 | Yang | B29D 11/00673 385/109 |
| 6,329,069 | B1 | 12/2001 | Azizi et al. | |
| 6,450,948 | B1 * | 9/2002 | Matsuura | A61B 1/0055 600/139 |
| 6,855,137 | B2 * | 2/2005 | Bon | A61M 25/0012 264/634 |
| 7,766,820 | B2 * | 8/2010 | Core | A61B 17/3439 600/140 |
| 7,824,392 | B2 * | 11/2010 | Zhou | A61M 25/005 604/523 |
| 8,216,498 | B2 | 7/2012 | Quillin | |
| 8,376,632 | B2 | 2/2013 | Blackburn et al. | |
| 8,540,760 | B2 | 9/2013 | Paul et al. | |
| 8,920,870 | B2 * | 12/2014 | Weber | A61M 25/0009 427/2.1 |
| 9,101,733 | B2 * | 8/2015 | McDaniel | A61B 18/1492 |
| 9,364,634 | B2 * | 6/2016 | Adams | A61M 25/0009 |
| 9,622,892 | B2 * | 4/2017 | Baker | A61F 2/962 |
| 9,855,095 | B2 * | 1/2018 | Howat | A61N 1/05 |
| 2002/0161353 | A1 * | 10/2002 | Kortelling | A61M 25/0141 604/528 |
| 2003/0004493 | A1 * | 1/2003 | Casey | A61M 25/005 604/525 |
| 2003/0028173 | A1 | 2/2003 | Forsberg | |
| 2005/0075626 | A1 * | 4/2005 | Venturelli | A61M 25/0012 604/524 |
| 2007/0010786 | A1 * | 1/2007 | Casey | A61B 17/22031 604/95.04 |
| 2008/0086047 | A1 | 4/2008 | McDaniel et al. | |
| 2008/0132633 | A1 * | 6/2008 | Topoulos | C08J 5/043 524/447 |
| 2009/0031269 | A1 | 1/2009 | Chen et al. | |
| 2009/0171348 | A1 * | 7/2009 | Guo | A61M 25/0052 606/41 |
| 2009/0312698 | A1 * | 12/2009 | Farrell | A61M 25/0009 604/95.04 |
| 2011/0172644 | A1 | 7/2011 | Zanoni et al. | |
| 2012/0008884 | A1 | 1/2012 | Murray | |
| 2012/0088846 | A1 * | 4/2012 | Lergenmueller | A61L 27/14 514/772.4 |
| 2012/0172714 | A1 | 7/2012 | Govari et al. | |
| 2012/0261857 | A1 | 10/2012 | Quillin | |
| 2012/0277671 | A1 | 11/2012 | Fuentes | |
| 2014/0023786 | A1 | 1/2014 | Hoff et al. | |
| 2015/0100043 | A1 | 4/2015 | Govari et al. | |
| 2016/0027136 | A1 | 1/2016 | Taketomo | |
| 2016/0271361 | A1 * | 9/2016 | Suzuki | A61M 25/0045 |
| 2018/0169378 | A1 * | 6/2018 | Laduca | A61L 29/12 |

FOREIGN PATENT DOCUMENTS

| | | |
|---|---|---|
| EP | 2732843 A1 | 5/2014 |
| WO | 9948548 A1 | 9/1999 |

* cited by examiner

EXTRUSION WITH PREFERENTIAL BEND AXIS

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to instruments for performing medical examinations of the interior of cavities or tubes of the body. More particularly, this invention relates to a medical catheter constructed by a process for applying fluent materials to a surface or part of a surface.

2. Description of the Related Art

It is common to map and ablate endocardial tissue in subjects having electrical conduction abnormalities. The procedures are performed with an elongate catheter having a lumen extending longitudinally through it. One technique, described in U.S. Pat. No. 5,993,462, involves inserting a core wire into a catheter via the lumen. The core wire includes a pre-shaped region. Such catheters includes a proximal section that is sufficiently rigid to straighten the core wire when the core wire is disposed within the proximal section. A distal section of the catheter is significantly more flexible than the proximal section.

Deflectable catheters are widely used for a variety of applications. In the area of electrophysiology. However, due to their inherent flexibility, catheters can be difficult to control as precisely as would be desired. Accordingly, a needs exists for a deflectable catheter having a mechanism to enhance the user's ability to control the degree and direction of deflection of the catheter. Moreover, it is desirable to provide preferential in-plane bidirectional deflection for cardiac catheters. Currently catheters of this sort are produced by extrusion. In-plane bidirectional deflection for an extrusion is achieved by using either a blade design or two polyimide struts that provides the extrusion a preferential bending along one axis. Both methods rely upon attaching a multi-lumen deflectable extrusion to the distal end of a single lumen shaft extrusion. Neither is compatible with a continuous process, whereby the shaft and deflectable part are made as one piece.

SUMMARY OF THE INVENTION

According to disclosed embodiments of the invention, a catheter is formed by an intermittent extrusion over the outer jacket of a braided multi-lumen catheter that produces variable degrees of hardness along its length. The intermittent extrusion is coupled with a coextrusion, whereby bands of a relatively stiffer resin are extruded along the outside of the shaft, opposite each other. On the proximal section of the shaft the stiffer resin is close in properties to the resin used on the outer jacket, so there is little preferential bending. On the distal section a larger difference between the stiff coextruded bands, and the relatively floppy jacket, allows for preferential in-plane bending.

Moreover, the process allows for the same multi-lumen configuration to extend along the entire length of the catheter, so that routed wires, tubes, and coils can never tangle. The process is less expensive than conventional methods. It completely eliminates the use of polyimide for stiffeners or deflection as well as eliminating a shrink sleeve, as no reflow steps are needed.

There is provided according to embodiments of the invention a method, which is carried out by coextruding a first molten polymer with a second molten polymer, wherein the second molten polymer forms a flexible inner core and the first molten polymer forms exactly two bands on opposite sides of the inner core, the bands being more rigid than the inner core. The method is further carried out by overlaying a braid on the inner core and the bands, and extruding a third molten polymer onto the braid to form a flexible jacket that encloses the braid, the bands and the inner core.

According to one aspect of the method, the first molten polymer is a polyamide.

According to one aspect of the method, the second and third molten polymer is polyether block amide and barium sulfate.

According to an additional aspect of the method, in a solid state the first molten polymer has a higher durometer than the second molten polymer.

According to yet another aspect of the method, the third molten polymer also includes a color concentrate.

A further aspect of the method is carried out during the coextrusion by changing a first composition of the third molten polymer to a second composition of the third molten polymer to define a proximal segment and a distal segment of a shaft and a transitional segment therebetween, the proximal segment being more rigid than the distal segment.

According to still another aspect of the method in the proximal segment the braid has a first configuration, in the distal segment the braid has a second configuration and in the transitional region the braid transitions between the first configuration and the second configuration. The first configuration offers more resistance to flexion of the shaft than the second configuration.

There is further provided according to embodiments of the invention an apparatus including a catheter shaft prepared by a process, which is carried out coextruding a first molten polymer with a second molten polymer, wherein the second molten polymer forms a flexible inner core and the first molten polymer forms exactly two bands on opposite sides of the inner core, the bands being more rigid than the inner core. The process is further carried out by overlaying a braid on the inner core and the bands, and coextruding a third molten polymer onto the braid to form a flexible jacket that encloses the braid, the bands and the inner core.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 1:
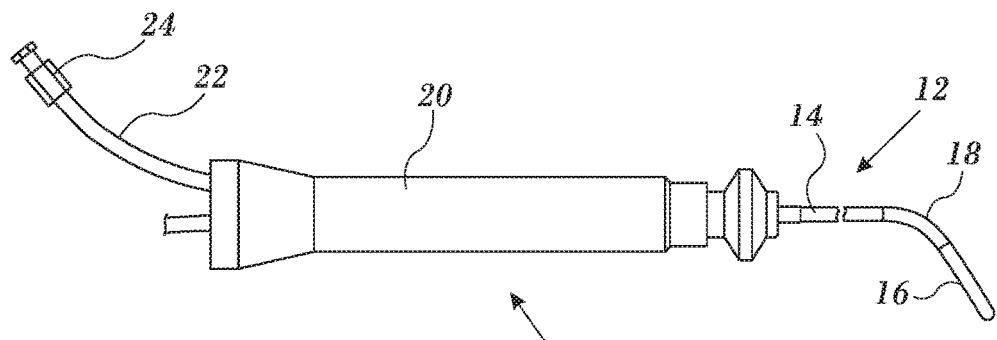
FIG. 1 is a schematic diagram of a medical catheter that can be constructed according to an embodiment of the invention.

Turning now to the drawings, reference is initially made to FIG. 1, which is a schematic diagram of a medical catheter 10 that can be constructed according to an embodiment of the invention. The catheter 10 comprises an elongated catheter shaft 12 having a proximal section 14, distal section 16 and an intermediate section 18. One or more electrodes or other devices are mounted on the distal section 16 for performing mapping, ablation or another desired function, and a control handle 20 is located at the proximal section 14 of the shaft 12. An infusion tube 22 is provided to introduce fluid through a lumen (not shown) of the shaft 12. A leer hub 24 is mounted on the proximal end of the infusion tube 22 to facilitate introduction of the fluid into the catheter 10.

Figure 2:
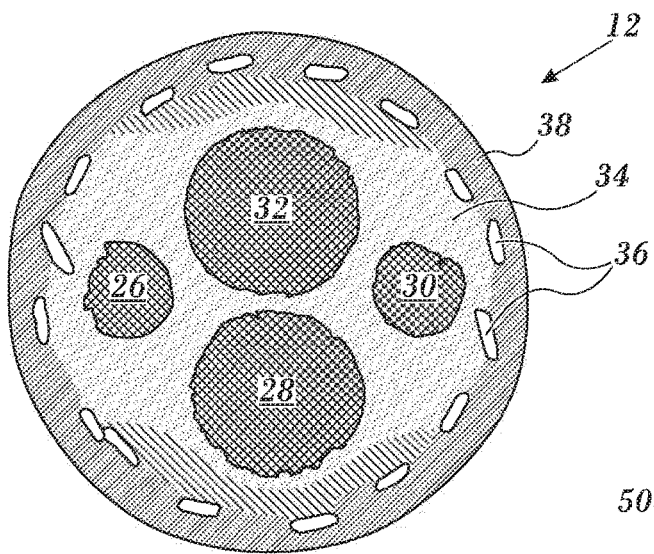
FIG. 2 is a cross sectional view of the shaft of the catheter shown in FIG. 1 in accordance with an embodiment of the invention.

Reference is now made to FIG. 2, which is a cross sectional view of the shaft 12 in accordance with an embodiment of the invention. The shaft is constructed by extrusion, as described in the detailed description below. In the depicted embodiment, the shaft 12 includes lumens 26, 28, 30, 32 surrounded by a relatively soft inner extrusion 34, which is drawn through a metallic braid 36. While 4 lumens are shown, a catheter may comprise more or fewer lumens, depending on the application intended.

The inner extrusion 34 and braid 36 are surrounded by an outer jacket 38, which is more rigid than the inner extrusion 34. As explained below the jacket 38 is most rigid in the proximal section 14 and least rigid in the distal section 16. The intermediate section 18, which is typically about 7 cm in length, forms a transitional zone having an intermediate rigidity.

Coextrusion.

Figure 3:
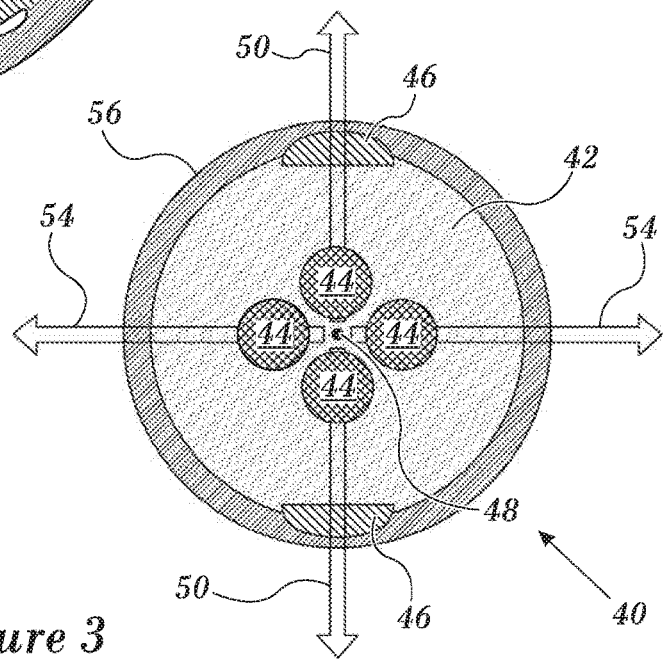
FIG. 3 is a schematic cross sectional view through a shaft of a catheter that was produced in accordance with an embodiment of the invention.

Reference is now made to FIG. 3, which is a schematic cross sectional view through a shaft 40 of a catheter that was produced in accordance with an embodiment of the invention. The coextrusion of the shaft 40 is done simultaneously. Two hoppers (each with its own resin) feed one die that takes the materials at one time and produces an extrusion with a circular outside diameter and having two bands 46 present to produce the structure shown in FIG. 3. In this example an inner extrusion 42 has four lumens 44.

The rigidity of bands 46 is greater than that of inner extrusion 42, which allows for preferential flexion of the outstretched shaft away from its longitudinal axis. The shaft 40 resists flexion maximally with respect to axis 48 in a direction of either of the bands 46 as indicated by arrows 50 and lessens as the bend angle deviates from that direction. Resistance to flexion is minimal when the direction of bending is perpendicular to a line connecting the two bands 46 as indicated by arrows 54. The resistance to bending creates a preferential bend plane for the shaft 40 and helps to overcome any undesired bend biases created by asymmetry in the lumen location or wall thicknesses. The lumens 44 are aligned with the arrows 54, i.e., on a diameter of the inner extrusion 42 that is perpendicular to diameter passing through the bands 46. This arrangement facilitates manipulation of the shaft by core wires inserted through the lumens 44 as described in the above-noted U.S. Pat. No. 5,993,462, because the forces produced by manipulation of the core wires are exerted primarily along the preferential bend plane.

The inner extrusion 42 and the bands 46 are braided with a braiding machine. After braiding, the shaft 40 is drawn through a second extruder that extrudes another molten polymer to form a jacket 56 over the braid. The extrusion of the jacket 56 can be performed by a process known as "Total Intermittent Extrusion" (TIE), which has been popularized by Putnam Plastics, 130 Louisa Viens Drive Dayville, Conn. 06241. This process is capable of producing extrusions with variable durometers along the length. It works by quickly switching between different resins according to a schedule. This allows the extruder to vary the stiffness of the jacket in small discrete steps, and hence, to vary the rigidity of the catheter shaft in a nearly continuous manner. Alternatively, if desired, sections (a proximal stiff section, and a distal floppy section for a catheter) can be cut out of the continuous spool produced by the extruders and rejoined to form the shaft of the catheter.

EXAMPLE

A catheter shaft may be produced by coextrusion as described above to the following specifications:
Bands: Vestamid® Care polyamide ML21)
Jacket (Polymer 60) Proximal Section
96%: pre-compounded:
50%: 80% polyether block amide (Pebax® 6333 Sa01 Med with 20% BaSo4 50%):
80% Pebax 7233 Sa01 Med with 20% BaSO4
4%:
PMS 3005c Color Concentrate Cs5916 (Blue)
Jacket (Polymer 60) Distal Section
96%: pre-compounded:
80% Pebax 4033 Sa01 Med with 20% BaSO4
4%:
PMS 2190CP Color Concentrate (Light Blue)
Inner Extrusion:
100%: Pre-Compounded, 80% Pebax 4033 Sa01 Med with 20% BaSO4.

Alternate Embodiment

In this embodiment coextrusion is performed using the procedure described with reference to FIG. 3, except that the TIE procedure need not be implemented. Instead a jacket of constant durometer in the range of 40 D-55 D is extruded by a suitable choice of the polymer. Variable stiffness in different sections the shaft is achieved by varying the characteristics of the braid.

Figure 4:
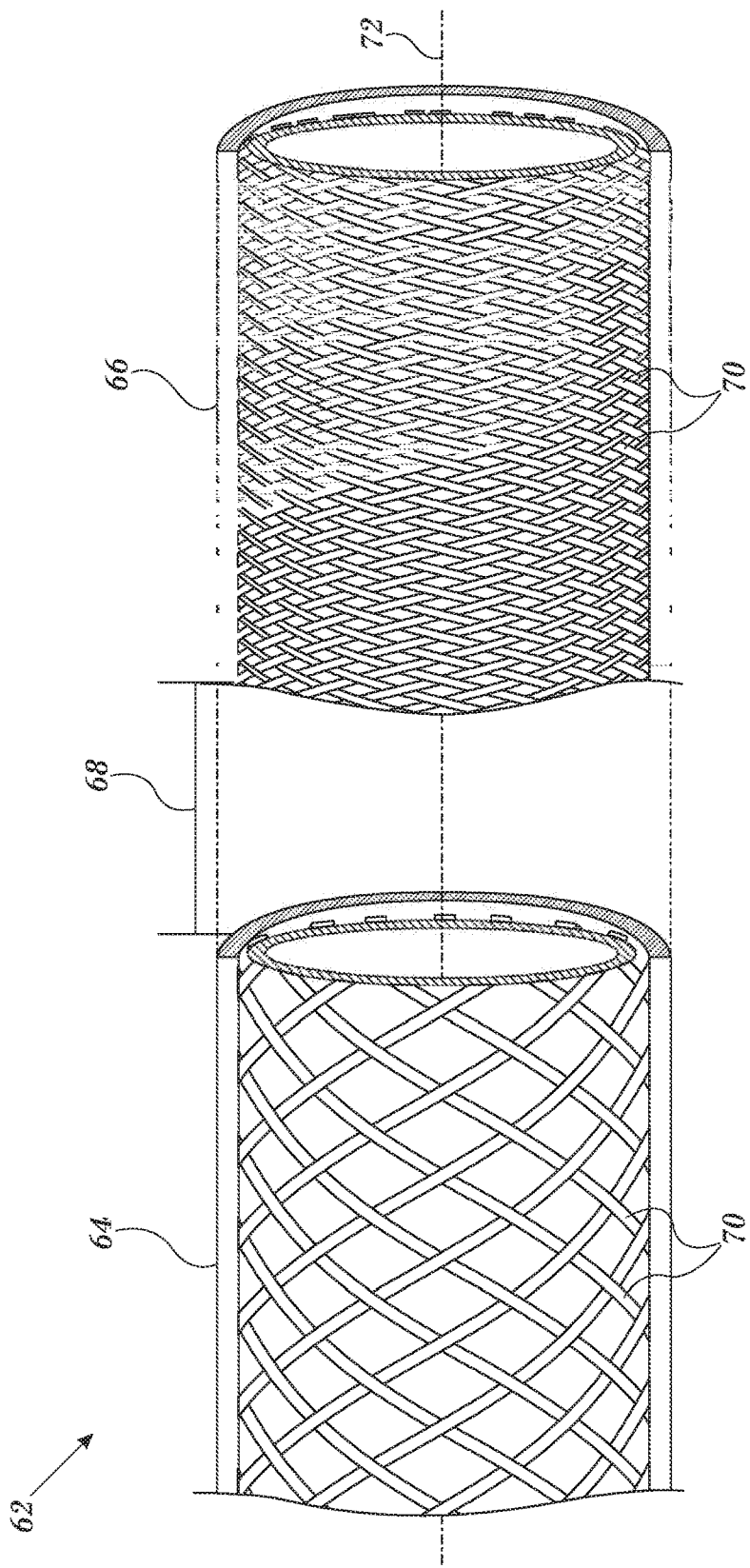
FIG. 4 is a diagram illustrating braids of a coextruded catheter shaft in accordance with an alternate embodiment of the invention.

Reference is now made to FIG. 4, which is a diagram illustrating braids of a catheter shaft 62 in accordance with an alternate embodiment of the invention. Proximal section 64 of the shaft 62 is shown on the left-hand-side of the figure; distal section 66 of the shaft 62 is shown on the right-hand-side, and a transition region 68 is shown in the middle of the figure, connecting the proximal and distal sections.

The braids comprise a set of wires 70 that are woven in a cross-braiding configuration. In the distal section, the density of the same set of wires 70 is increased, increasing the braid angle and making the distal section more axially compliant at the expense of torque. Selective directional rigidity is provided by the bands (not shown in FIG. 4) as in the previous embodiment.

Both proximal section 64 and distal section 66 transfer rotational torque about the catheter axis 72 to the catheter distal tip, enabling the operator to rotate the catheter as desired.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
   coextruding a first molten polymer with a second molten polymer, wherein the second molten polymer forms a flexible inner core and the first molten polymer forms exactly two bands partially inside of and on opposite sides of the inner core, the bands being more rigid than the inner core;
   overlaying a braid on the inner core and the bands;
   coextruding a third molten polymer onto the braid to form a jacket that encloses the braid, the bands and the inner core; and
   while performing the step of coextruding the third molten polymer, changing a first composition of the third molten polymer to a second composition of the third molten polymer to define a proximal segment and a distal segment of a shaft and a transitional segment therebetween, the proximal segment being more rigid than the distal segment.

2. The method according to claim 1, wherein in the proximal segment the braid has a first configuration, in the distal segment the braid has a second configuration and in the transitional segment the braid transitions between the first configuration and the second configuration, wherein the first configuration offers more resistance to flexion of the shaft than the second configuration.

3. The method according to claim 1, wherein the third molten polymer comprises polyether block amide and barium sulfate.

4. The method according to claim 1, wherein the third molten polymer comprises a color concentrate.

5. The method according to claim 1, wherein the first molten polymer comprises a polyamide.

6. The method according to claim 1, wherein in a solid state the first molten polymer has a higher durometer than the second molten polymer.

7. The method according to claim 1, wherein the inner core has two lumens formed therethrough, the lumens being aligned on a diameter of the inner core that is perpendicular to a diameter passing through the bands and dimensioned to accept core wires.

* * * * *